United States Patent [19]

Laue et al.

[11] Patent Number: 5,204,238

[45] Date of Patent: Apr. 20, 1993

[54] PROCESS FOR THE REDUCTION OF STAR ACTIVITIES

[75] Inventors: Frank Laue, Pähl; Waltraud Ankenbauer, Penzberg; Gudrun Schmitz, Bernried, all of Fed. Rep. of Germany

[73] Assignee: Boehringer Mannheim GmbH, Mannheim, Fed. Rep. of Germany

[21] Appl. No.: 669,562

[22] Filed: Mar. 14, 1991

[30] Foreign Application Priority Data

Mar. 26, 1990 [DE] Fed. Rep. of Germany ....... 4009663

[51] Int. Cl.$^5$ .......................... C12Q 1/68; C12N 9/24
[52] U.S. Cl. ......................................... 435/6; 435/199
[58] Field of Search ........................... 435/6, 199, 184; 424/94.5

[56] References Cited

PUBLICATIONS

Pingoud, A. (1985) European Journal of Biochemistry vol. 147, pp. 105-109.

White, R. J. et al. (1989) Biochemistry, vol. 28, pp. 6259-6269.

Kopka, M. L. et al. (1985) P.N.A.S., vol. 82, pp. 1376-1380.

Low, C. M. L. et al. (1984) Nucleic Acids Research, vol. 12, pp. 4865-4879.

Berman, H. M. et al (1979) Biochimica and Biophysica Acta vol. 561, pp. 124-131.

*Primary Examiner*—Margaret Moskowitz
*Assistant Examiner*—Lisa Bennett
*Attorney, Agent, or Firm*—Nikaido, Marmelstein, Murray & Oram

[57] ABSTRACT

The present invention provides a process for the reduction of non-specific star activities in the case of the specific cleavage of desoxyribonucleic acids by incubation with a restriction endonuclease in an appropriate buffer, wherein to the incubation batch is added an antibiotic which binds to the DNA on or near the star sequences of the enzyme but not within the specific recognition sequence of the restriction endonuclease.

9 Claims, No Drawings

PROCESS FOR THE REDUCTION OF STAR ACTIVITIES

The present invention is concerned with a process for the reduction of non-specific star activities in the case of the specific cleavage of desoxyribonucleic acids by incubation with a restriction endonuclease in an appropriate buffer.

For almost 20 years, restriction enzymes have been used for the cleavage of desoxyribonucleic acids. The so-called type II restriction endonucleases thereby recognised specific sequences of double-stranded DNA and cleave the DNA within these recognition sequences. However, in the case of many restriction endonucleases, under certain incubation conditions, the specificity is reduced and they exhibit the so-called "star activity". Sequences which, in the following, are called star sequences, are thereby cleaved which are similar to the recognition sequence but are not identical with them (see B. Polisky, P. Greene, D. E. Garfin, B. J. McCarthy, H. M. Goodman and H. W. Boyer, Proc. Natl. Acad. Sci. U.S.A., 22, 3310/1975). Such star activities have been ascertained for many enzymes, for example EcoRI (EcoRI*). Since the star activity is a property inherent to the enzyme, it also cannot be avoided by a further purification of the enzyme preparation. In general, star activity is especially to be observed when high endonuclease concentrations, long incubation times, low ionic strength, high pH value, low temperatures and organic solvents, for example dimethyl sulphoxide or glycerol, are used which destabilise the double-stranded DNA structure.

Attempts have admittedly been made to suppress the star activity by increasing the ionic strength but this frequently involves a loss of the enzyme activity.

A further possibility for suppressing the star activity is the addition of spermidine to the incubation batch (see A. Pingoud, Eur. J. Biochem., 147, 105–109/1985). However, the specific activity is thereby also reduced. Even under these conditions, in the case of some enzymes star activity is still observed.

Therefore, it is an object of the present invention to provide a process which, without a reduction of the specific enzyme activity, permits the non-specific star activities of restriction endonucleases to be substantially reduced and which can be used universally under conventional incubation conditions.

Therefore, according to the present invention, there is provided a process for the reduction of non-specific star activities in the case of the specific cleavage of desoxyribonucleic acids by incubation with a restriction endonuclease in an appropriate buffer, wherein to the incubation batch there is added an antibiotic which binds to the DNA on or near the star sequences of the enzyme but not within the specific recognition sequence of the restriction endonuclease.

The process according to the present invention is carried out under standard conditions for the particular restriction enzyme used, namely, preferably in a pH range of 7.5 to 8.0 in the case of Tris-acetate or Tris-HCl concentrations of 10 to 50 mmole/liter, magnesium acetate or magnesium chloride in concentrations of 5 to 10 mmole/liter, potassium acetate of 66 mmole/liter or sodium chloride in concentrations of from 0 to 100 mmole/liter. As reduction agents there can be used DTE (1,4-dithioerythritol, 1 mmole/liter), DTT (1,4-dithiothreitol, 0.5 mmole/liter) or 2-mercaptoethanol (1 mmole/liter). Especially preferred conditions are described in the brochure of the firm Boehringer Mannheim GmbH "Biochemicals for Molecular Biology", pages 176–177/1988 and a similar form by Maniatis et al., Molecular Cloning, A Laboratory Manual, Cold Spring Harbor Laboratory, 1982, as well as by O'Farrell et al., Mol. Gen. Genet., 179, 421/1980. In each case, especially suitable buffer compositions are given for a large number of restriction enzymes.

By means of the addition of the DNA-binding antibiotic, the star activities are clearly reduced even if not completely overcome. This takes place by binding of the antibiotic on to or near the star sequences of the restriction enzyme on the DNA which thus protects the sequences against cleavage. However, it is important for the process according to the present invention that a binding of the specific recognition sequence of the restriction enzyme by the antibiotic also does not take place since the specific activity would thereby also be strongly impaired.

In order to find an appropriate antibiotic reducing the star activity but which does not impair the specific activity of the enzyme, according to the present invention two kinds of orientation experiments are to be carried out. In the first place, it must be ensured that the antibiotic used does not bind to the specific recognition sequence of the restriction endonuclease. For this purpose, there is preferably carried out a so-called "footprint assay" (see R. J. White and D. R. Phillips, Biochemistry, 28, 6259–6269/1989; W. S. Dynan and R. Tjian, Cell, 35, 79–87/1983). According to this method, the DNA-binding antibiotic is bound to a DNA fragment which contains at least once the specific recognition sequence of the restriction endonuclease and the DNA is then broken down with DNAse in such a manner that at most one cleavage occurs per DNA fragment. In the case of the separation of the cleavage products in the denatured polyacrylamide gel, there results a ladder-like pattern in which holes are there found where the binding protein has protected the DNA against cleavage by DNAse. On the same gel, there are applied next thereto the various batches of a sequencing according to Maxam-Gilbert, it thereby being possible precisely to ascertain the position of the recognition sequence and the possible binding thereof by the antibiotic.

As further orientation experiment, it must also be tested whether the antibiotic used indeed reduces the star activities of the restriction endonuclease. This takes place in that, in parallel, the DNA to be cleaved is incubated in batches, in each case with and without antibiotic. After separation of the resultant fragments in an agarose gel, it can be ascertained whether, after the addition of antibiotic, the bands appearing in the gel on the basis of the star activities are reduced or removed.

However, the possibility also exists, in the process according to the present invention, to make use of antibiotics, the preferred binding sequence of which is already known. Such antibiotics are preferably used in the process according to the present invention. The following Table 1 shows a list of preferred antibiotics, the binding sequence thereof, as well as the literature references in which these antibiotics are described in more detail. On the basis of the known binding sequences of these antibiotics, it can easily be ascertained whether the antibiotic is appropriate for reducing the star activities and/or whether it is to be expected that the specific activity will be impaired by binding of the antibiotic to the specific recognition sequence of the restriction endonuclease.

TABLE 1

| antibiotic | preferred binding sequence | literature |
|---|---|---|
| actinomycin D | GC | 1, 2 |
| distamycin | ATT or AATT | 1, 3 |
| echinomycin | CG | 1, 4 |
| mithramycin | GC | 1 |
| netropsin | A/T A/T A/T | 5, 6 |

1. R. J. White and D. R. Phillips, Biochemistry, 28, 6259–6269/1989
2. V. A. Aivasashvilli and R. S. Beabealashvilli, FEBS Lett., 160, 12–128/1983
3. M. L. Kopka, C. Yoon, D. Goodsell, O. Pjura and R. E. Dickerson, Proc. Natl. Acad. Sci. USA, 82, 1376–1380/1985
4. C. M. L. Low, H. R. Drew and M. J. Waring, Nucl. Acids Res., 12, 4865–4879/1984
5. H. M. Berman, S. Neidle, C. Zimmer and H. Thrum, Biochim. Biophys. Acta, 561, 124–131
6. A. D. B. Malcolm and J. R. Moffat, Biochim. Biophys. Acta, 655, 128–135/1981.

Whether a particular restriction enzyme displays star activities is easy to determine on the basis of the cleavage of known DNA sequences which have a definite number of DNA sequences of the enzyme. If, after cleavage of this known DNA sequence by the enzyme has taken place, unexpected bands appear in the gel, then this is due to a star activity. In the following Table 2, for some enzymes of which it is known that they possess star activities of a more or less strong extent, there is given the recognition sequence of the enzyme, as well as one or more antibiotics which can be used for the reduction of the star activities, together with the preferred binding sequences thereof.

TABLE 2

| Enzyme | recognition sequence of the enzyme | antibiotic | preferred binding sequence of the antibiotic |
|---|---|---|---|
| EcoRI | GAATTC | actinomycin D | GC |
| SgrAI | C A CCGG T G<br>  G        C | netropsin | A/T A/T A/T |
| BamHI | GGATCC | actinomycin D | GC |
|  |  | mithramycin | GC |
| BfrI | CTTAAG | actinomycin D | GC |
| EcoRV | GATATC | actinomycin D | GC |
|  |  | mithramycin | GC |
| HaeIII | GGCC | netropsin | A/T A/T A/T |
|  |  | distamycin | ATT or AATT |
| HhaI | GCGC | netropsin | A/T A/T A/T |
|  |  | distamycin | ATT or AATT |
| HindIII | AAGCTT | echinomycin | CG |
| HpaI | GTTAAC | actinomycin D | GC |
| PaeR7 | CTCGAG | netropsin | A/T A/T A/T |
| PstI | CTGCAG | " | " |
| PvuII | CAGCTG | " | " |
| SalI | GTCGAC | " | " |
| SstI | GAGCTC | " | " |
| XbaI | TCTAGA | echinomycin | CG |
|  |  | actinomycin D | GC |

The given combinations of restriction endonuclease and antibiotic are preferred embodiments of the process according to the present invention. However, other combinations of enzyme and antibiotic can also be used in the process according to the present invention, so long as it has been ascertained by the above-described orientation experiments that the star activities are admittedly reduced but the specific activity of the restriction endonuclease is not significantly changed.

In the process according to the present invention, the antibiotics are preferably used in an amount of from 5 to 200 μmole/liter in the incubation batch.

The process according to the present invention makes it possible, in a simple manner, in the case of cleavage of desoxyribonucleic acids by restriction endonucleases of type II, to increase the specificity of the cleavage in that non-specific star activities of the enzyme are reduced by binding of an antibiotic to the star sequences of the enzyme on the DNA. Preferred antibiotics can thereby be taken either from the preferred combinations of enzyme and antibiotic given by way of example or can also be determined by simple preliminary experiments. Thus, in a simple and cost-favourable manner, it is possible to carry out an extremely specific DNA cleavage which is highly desirable for today's gene-technological methods but which hitherto it has not been possible to achieve with all enzymes.

The following Examples are given for the purpose of illustrating the present invention:

EXAMPLE 1

Determination of the Activity and Detection of the Star Activity for SgrAI a) Activity Definition of the enzyme units 1 U SgrAI cleaves 1 μg. of lambda-DNA within 1 hour at 37° C. in a 50 μl. end volume.

For the determination of the activity, increasing amounts of enzyme (different dilutions) are incubated with 1 μg. lambda-DNA. The amount of enzyme which completely cleaves 1 μg. lambda-DNA in 1 hour at 37° C. corresponds to 1 U.

b) Activity test

To a mixture of 5 μl. of incubation buffer (330 mmole/liter Tris-acetate, pH 7.9/37° C., 100 mmole/liter magnesium acetate, 660 mmole/liter potassium acetate and 5 mmole/liter DTT) are added 39 μl. (if netropsin is added to the reaction mixture, 35 μl.) of water and 5 μl. lambda-DNA (optical density: 4 OD/ml.), as well as 1 μl. of SgrAI (0.2 U/μl. to 15 U/μl.). The solution is incubated for 1 hour at 37° C., cooled on ice and mixed with 10 μl. of a stop reagent, consisting of 7 mole/liter urea, 20% (w/v) of saccharose, 60 mmole/liter EDTA and 0.01% (w/v) bromophenol blue. Subsequently, a separation is carried out by electrophoresis in 0.8% agarose gels for 2 to 3 hours at 100 volts. The bands obtained are identified by comparison with a DNA length standard.

c) Detection of star activity

The star activity is characterised by the appearance of bands which appear in addition to the band pattern of the complete digestion arising by specific cleavage.

The preparation of the incubation mixture and the analysis of the cleavage products takes place analogously to the activity test. However, the period of incubation is 16 hours.

EXAMPLE 2

Determination of the Activity and Detection of the Star Activity for EcoRI a) Activity Definition of the enzyme units 1 U EcoRI cleaves 1 μg. of lambda-DNA within 1 hour at 37° C. in a 25 μl. end volume.

For the determination of the activity, increasing amounts of enzyme (different dilutions) are incubated with 1 μg. lambda-DNA. The amount of enzyme which completely cleaves 1 μg. lambda-DNA in 1 hour at 37° C. corresponds to 1 U.

b) Activity test

To a mixture of 2.5 μl. of incubation buffer (500 mmole/liter Tris-HCl, pH 7.5/37° C., 1 mole/liter sodium chloride, 100 mmole/liter magnesium chloride and 10 mmole/liter DTE) are added 16.5 μl. (when the activity is to be determined in the presence of antibiotics, 14 μl.) of water and 5 μl. lambda-DNA (optical density: 4 OD/μl.), as well as 1 to 2 μl. EcoRI solution (0.3 to 40 U/μl.). The solution is incubated for 1 hour at 37° C., cooled on ice and mixed with a stop reagent, consisting of 7 mole/liter urea, 20% (w/v) saccharose, 60 mmole/liter EDTA and 0.01% (w/v) bromophenol blue. Subsequently, there is carried out a separation by electrophoresis in 0.8% agarose gels for 2 to 3 hours at 100 volts. The bands obtained are identified by comparison with a DNA length standard.

c) Detection of star activity

The star activity is characterised by the appearance of bands which occur in addition to the band pattern of the complete digestion arising by specific cleavage.

The reaction mixture is prepared by the same process as described for the determination of the activity. However, the incubation time is 16 hours. The separation of the cleavage products also takes place as described in the case of the determination of activity.

EXAMPLE 3

Detection Which Binds Netropsin Outside of the Recognition Sequence of SgrAI

With the use of the "footprinting" method (see R. J. White and D. R. Phillips, Biochemistry, 28, 6259–6269/1989; W. S. Dynan and R. Tjian, Cell, 35, 79–87/1983) it is investigated whether netropsin binds outside of the recognition sequence for SgrAI. According to this method, DNA-binding factors are bound to DNA fragments and these are then digested with DNAse in such a manner that, at most, one cleavage results per fragment. In the case of separation of the cleavage products in denatured polyacrylamide gel, a ladder-like pattern results. In these ladders, holes are present where the binding protein has protected the DNA against cleavage by DNAse. A fragment with a length of 191 base pairs, which contains a cleavage position for SgrAI, is cut out with BamHI and SphI from the plasmid pBR322 and labelled with $^{32}$phosphorus on the BamHI cleavage position. In each case, 5 fmole of this fragment are incubated with 10 μmole/liter and 20 μmole/liter of netropsin and cleaved with DNAseI. After separation of the cleavage products in a polyacrylamide gel, several protected regions are detected. However, the recognition sequence for SgrAI is not protected by netropsin.

EXAMPLE 4

Examples in which antibiotics which bind to the recognition sequence do not influence the star activity or, apart from the star activity, also reduced the specific activity.

The determination of the activity takes place for SgrAI as described in Example 1 and for EcoRI as described in Example 2.

The specific activity of SgrAI, which has a binding position for actinomycin D in the recognition sequence, is inhibited by actinomycin D (>6 μmole/liter.

The specific activity of EcoRI, which has a binding position for netropsin in the recognition sequence, is inhibited by netropsin (200 μmole/liter).

The specific activity and the star activity of ScaI, which also has a binding position for netropsin in the recognition sequence, is inhibited by netropsin (<150 μmole/liter).

Activity Determination of ScaI

Definition of the enzyme units

1 U ScaI cleaves 1 μg. of lambda-DNA within 1 hour at 37° C.

To a mixture of 2,5 μl. incubation buffer (500 mmole/liter Tris-HCl, pH 7.5/37° C., 100 mmole/liter magnesium chloride, 1 mole/liter sodium chloride and 10 mmole/liter DTE) are added 17.5 μl. water and 5 μl. lambda-DNA (optical density: 4 OD/μl.), as well as 1 μl. ScaI solution (1U/μl.–5 U/μl.). The solution is incubated for 1 hour at 37° C., cooled on ice and mixed with 5 μl. of a stop reagent consisting of 7 mole/liter urea, 20% (w/v) saccharose, 60 mmole/liter EDTA and 0.01 (w/v) bromophenol blue. Subsequently, a separation is carried out by electrophoresis in 1% agarose gels for 2 to 3 hours at 100 volts. The bands obtained are identified by comparison with a DNA length standard.

EXAMPLE 5

Detection of the Binding of an Antibiotic to the Recognition Sequence or Outside Thereof Such a method is the footprinting method which is described in Example 3.

DNA-binding antibiotics are bound to DNA fragments in concentrations of 5 to 20 μmole/liter. These DNA fragments are to contain the RE recognition sequences to be investigated. The DNA fragments are terminally labelled with $^{32}$phosphorus on one of the two strands. In each case, 5 to 10 fmole of labelled fragment are incubated for 15 minutes at 0° C. in a reaction volume of 50 μl. with 2 to 20 μmole/liter of antibiotic. Thereafter, the reaction batch is incubated for 1 minute at ambient temperature, 50 μl. of a solution of magnesium chloride (10 mmole/liter) and calcium chloride (5 mmole/liter) are added thereto and again incubated for 1 minute at ambient temperature. 2 μl. DNAse (0.125 ng./ml.) are added thereto and incubated for 1 minute at ambient temperature. The reaction is stopped by the addition of 90 μl. of stop solution (20 mmole/liter EDTA, 1% SDS, 0.2 mmole/liter sodium chloride and 250 μg./ml. yeast RNA; pH 8.0). The reaction mixture is phenolised and the DNA is precipitated with ethanol and separated on a 6% polyacrylamide gel which contains 8 mole/liter urea. The detection of the DNA takes place by autoradiography. The regions protected by the binding of the antibiotic are characterised by holes in the fragment ladders resulting by the limited DNAse digestion. The association of the binding positions to the sequence of the DNA fragment takes place by parallel-applied sequence ladders which are produced according to the process of Maxam and Gilbert (see Methods in Enzymology, 65, 497–559/1980).

EXAMPLE 6

Reduction of the Star Activity of SgrAI by Netropsin

The determination of the activity and star activity of SgrAI in the presence of netropsin takes place in the manner described in Example 1. To the incubation mixture are added 1.25 to 5 μl. of a solution of netropsin (4 mmole/liter netropsin, 10 mmole/liter Tris-HCl and 1 mmole/liter EDTA; pH 8.0). The star activity is characterised by the appearance of DNA fragments which occur in addition to those produced by the specific activity.

Conditions of the digestion

1 μg. Lambda-DNA, 0.1 to 0.4 mmole/liter netropsin, 1 to 20 U SgrAI, 33 mmole/liter Tris-acetate, 10 mmole/liter magnesium acetate, 66 mmole/liter potassium acetate, 0.5 mmole/liter DTT, pH 7.9 at 37° C. Volume of the reaction mixture 50 μl. Incubation for 16 hours at 37° C.

By cleavage of lambda-DNA with SgrAI on the recognition sequences CA/GCCGGC/TG, there result 7 fragments with 16676, 14850, 7066, 4198, 2775, 1616 and 1321 base pairs. These are separated by electrophoresis and made visible in ultra-violet light by staining with ethidium bromide.

Increasing amounts of SgrAI were, in each case, incubated with 1 μg. lambda-DNA for 16 hours at 37° C.

In the absence of netropsin, in the case of amounts of enzyme of from 1 to 5 U, there is to be observed the characteristic pattern (seven bands) for the complete digestion. With 7 U, the fragment with 1616 bp is partly degraded. With 10 U, additional bands of weaker intensity occur with which can be associated fragments with about 13,000 bp and about 10,500 bp. With 12 U SgrAI, the fragments with about 13,000 bp and 10,500 bp are clearly visible and further fragments with about 3800, 3700 and 2000 bp are formed but the fragment with 1616 bp is completely absent. With 16 U SgrAI, further additional fragments are formed, whereas the fragments resulting by the specific digestion are more strongly degraded.

In the case of the addition of 0.2 mmole/liter netropsin, up to 16 U SgrAI, no bands produced by star activity are to be observed. With 0.4 mmole/liter netropsin, even up to 16 U, no additional fragments are visible which could have resulted due to star activity and the fragment with 1616 bp is only slightly degraded.

The star activity can be reduced 2 to 3 fold by netropsin.

EXAMPLE 7

Reduction of the Star Activity of EcoRI by Actinomycin D

The determination of the activity and star activity of EcoRI in the presence of actinomycin D takes place analogously to the process described in Example 2. However, to the incubation batch are added 1.25 to 2.5 μl. of a solution of actinomycin D (200 μmole/liter actinomycin D, 10 mmole/liter Tris-HCl and 1 mmole/liter EDTA; pH 8.0) in TE.

Specific cleavage of lambda-DNA on the complete recognition sequence of EcoRI leads to fragments with 21226, 7421, 5804, 5643, 4878 and 3530 base pairs.

Conditions of the digestion 1 g. Lambda-DNA, 10 to 20 μmole/liter actinomycin D, 1 to 60 U EcoRI, 50 mmole/liter Tris-HCl, 10 mmole/liter magnesium chloride, 100 mmole/liter sodium chloride, 1 mmole/liter DTE; pH 7.5 at 37° C. Volume of the reaction mixture 25 μl. Incubation for 16 hours at 37° C.

When 1 μg. lambda-DNA is incubated for 16 hours with increasing amounts of EcoRI, the following observations are made: 1 to 10 U EcoRI give the complete digestion pattern of lambda-DNA. With 20 U EcoRI, additional bands occur which can be associated with fragments of the approximate size of 11500, 8800, 4500, 2800 and 2000 base pairs. The fragments resulting by the specific cleavage are partly degraded, as can be seen from the relative intensity. With 30 U EcoRI, the fragments characteristic for specific cleavage are further degraded and the fragments resulting by non-specific cleavage are more numerous and are present in a comparatively large amount.

However, if actinomycin D (10 μmole/liter) is added to the reaction mixture, the cleavage patterns, which are identical with the cleavage arising by 10 U, 20 U and 30 U EcoRI, only occur on the specific recognition sequence of EcoRI. Additional bands first occur with 40 U EcoRI. The star activity is reduced 3 fold.

We claim:

1. Process for the reduction of nonspecific star activities during the specific cleavage of deoxyribonucleic acids comprising incubation with a restriction endonuclease in an appropriate buffer, wherein an antibiotic which binds to the DNA on or near the star sequences of the enzyme but not within the specific recognition sequence of the restriction endonuclease is added to the incubation batch.

2. Process according to claim 1, wherein a footprint assay is carried out to determine whether an antibiotic binds to the specific recognition sequence of the restriction endonuclease, and the binding of the antibiotic to star sequences is ascertained by comparative experiments for the DNA cleavage with the endonuclease with and without antibiotic in the incubation batch.

3. Process according to claim 1, wherein said antibiotic is selected from the group consisting of antinomycin D, distamycin, echinomycin, mithramycin and netropsin.

4. Process according to claim 1, wherein said antibiotic is actinomycin D and said restriction endonuclease is selected from the group consisting of BamHI, BfrI, EcoRV, HpaI and Xba I.

5. Process according to claim 1, wherein said antibiotic is mithramycin and said restriction endonuclease is BamHI or EcoRV.

6. Process according to claim 1, wherein said antibiotic is netropsin and said restriction endonuclease is selected from the group consisting of HaeII, HhaI, PaeR7, PstI, PvuII, SalI and SstI.

7. Process according to claim 1, wherein said antibiotic is distamycin and said restriction endonuclease is HaeIII or HhaI.

8. Process according to claim 1, wherein said antibiotic is echinomycin and said restriction endonuclease is HindIII or XbaI.

9. Process according to claim 1, wherein the antibiotic is added to the batch in an amount of from 5 to 200 μmole/liter.

* * * * *